United States Patent
Nieskens et al.

(10) Patent No.: US 11,208,363 B2
(45) Date of Patent: Dec. 28, 2021

(54) CATALYST AND METHOD FOR CONVERTING CARBON-CONTAINING STREAM TO C2 TO C5 PARAFFINS USING IT

(71) Applicant: Dow Global Technologies LLC, Midland, MI (US)

(72) Inventors: Davy L. S. Nieskens, Terneuzen (NL); Glenn Pollefeyt, Wondelgem (BE); Andrzej Malek, Midland, MI (US); Edward M. Calverley, Midland, MI (US); Peter E. Groenendijk, Hulst (NL); Aysegul Ciftci Sandikci, Eindhoven (NL)

(73) Assignee: Dow Global Technologies LLC, Midland, MI (US)

( * ) Notice: Subject to any disclaimer, the term of this patent is extended or adjusted under 35 U.S.C. 154(b) by 0 days.

(21) Appl. No.: 16/967,599

(22) PCT Filed: Feb. 7, 2019

(86) PCT No.: PCT/US2019/016952
§ 371 (c)(1),
(2) Date: Aug. 5, 2020

(87) PCT Pub. No.: WO2019/168642
PCT Pub. Date: Sep. 6, 2019

(65) Prior Publication Data
US 2021/0087120 A1    Mar. 25, 2021

Related U.S. Application Data

(60) Provisional application No. 62/635,831, filed on Feb. 27, 2018.

(51) Int. Cl.
| | | |
|---|---|---|
| *C07C 1/04* | (2006.01) | |
| *B01J 21/02* | (2006.01) | |
| *B01J 23/26* | (2006.01) | |
| *B01J 23/80* | (2006.01) | |
| *C07C 1/12* | (2006.01) | |

(52) U.S. Cl.
CPC ............... *C07C 1/043* (2013.01); *B01J 21/02* (2013.01); *B01J 23/26* (2013.01); *B01J 23/80* (2013.01); *C07C 1/12* (2013.01); *B01J 2523/17* (2013.01); *B01J 2523/27* (2013.01); *B01J 2523/31* (2013.01); *B01J 2523/67* (2013.01)

(58) Field of Classification Search
CPC .. C07C 1/043; C07C 9/06; C07C 9/08; C07C 1/12; C07C 2529/83; C07C 2521/04; C07C 2529/70; C07C 2523/80; C07C 2523/26; C07C 2523/72; C07C 2529/85; B01J 23/26; B01J 35/026; B01J 37/04; B01J 35/0006; B01J 23/80; B01J 29/85; B01J 29/005; B01J 37/031
See application file for complete search history.

(56) References Cited

U.S. PATENT DOCUMENTS

| | | |
|---|---|---|
| 5,389,689 A | 2/1995 | Kaoru et al. |
| 5,466,720 A | 11/1995 | Kaoru et al. |
| 6,376,562 B1 | 4/2002 | Ihm et al. |
| 9,545,619 B2 | 1/2017 | Wang et al. |
| 2017/0210679 A1 | 7/2017 | Chojecki et al. |

FOREIGN PATENT DOCUMENTS

| | | |
|---|---|---|
| EP | 164156 A1 | 12/1985 |
| WO | 2016007607 A1 | 1/2016 |
| WO | 2018093880 A1 | 5/2018 |
| WO | 2019089206 A1 | 5/2019 |

OTHER PUBLICATIONS

International Search Report and Written Opinion pertaining to PCT/US2019/016952, dated Jul. 9, 2019.
Fujiwara et al., "Development of composite catalysts made of Cu—Zn—Cr oxide/zeolite for the hydrogenation of carbon dioxide", Applied Catalysis A: General, 1995, 121, 113-124.
Fujiwara et al., "Hydrocarbon Synthesis from Carbon Dioxide and Hydrogen over Cu—Zn—Cr Oxide/Zeolite Hybrid Catalysts", J.. Chem. Soc., Chem. Commun., 1992, 767-768.
Inui et al., "Hydrogenation of Carbon Dioxide to C1-C7 Hydrocarbons via Methanol on Composite Catalysts", Applied Catalysis A: General, 1993, 94, 31-44.
Calverley et al., "Synthesis of Higher Alcohols over Promoted Copper Catalysts", Journal of Catalysis, 1987, 104, 434-440.

(Continued)

*Primary Examiner* — Jafar F Parsa
(74) *Attorney, Agent, or Firm* — Dinsmore & Shohl LLP

(57) ABSTRACT

A process for preparing $C_2$ to $C_5$ paraffins includes introducing a feed stream comprising hydrogen gas and a carbon-containing gas into a reaction zone of a reactor, and converting the feed stream into a product stream comprising $C_2$ to $C_5$ paraffins in the reaction zone in the presence of a hybrid catalyst. The hybrid catalyst includes a metal oxide catalyst component and a microporous catalyst component. The metal oxide catalyst component satisfies: an atomic ratio of Cu/Zn from 0.01 to 3.00; an atomic ratio of Cr/Zn from 0.01 to 1.50; and percentage of (Al+Cr) from greater than 0.0 at % to 50.0 at % based on a total amount of metal in the metal oxide catalyst component.

8 Claims, No Drawings

(56) References Cited

OTHER PUBLICATIONS

Venugopal et al., "Cu—Zn—Cr2O3 Catalysts for Dimethyl Ether Synthesis:Structure and Activity Relationship", Catal. Lett., 2008, 123, 142-149.

Yan et al., "Effect of Cr promoter on performance of steam reforming of dimethyl ether in a metal foam micro-reactor", International Journal of Hydrogen Energy, 2014, 39, 18625-18631.

Kuhl et al., "Ternary and quaternary Cr or Ga-containing ex-LDH catalysts—Influence of the additional oxides onto the microstructure and activity of Cu/ZnAl2O4 catalysts", Catalysis Today, 2015, 246, 92-100.

Hua et al., "Single-step synthesis of dimethyl ether from biomass-derived syngas over CuO—ZnO—MOx (M =Zr, Al, Cr, Ti)/HZSM-5 hybrid catalyst: Effects of MOx", Applied Catalysis A, General, 2017, 540, 68-74.

CATALYST AND METHOD FOR CONVERTING CARBON-CONTAINING STREAM TO C2 TO C5 PARAFFINS USING IT

CROSS REFERENCE TO RELATED APPLICATIONS

This application is a National Stage Entry under 35 U.S.C. § 371 of International Patent Application No. PCT/US2019/016952, filed Feb. 7, 2019, which claims priority to U.S. Provisional Patent Application No. 62/635,831, filed Feb. 27, 2018, the contents of which are hereby incorporated by reference in their entireties.

BACKGROUND

Field

The present specification generally relates to a hybrid catalyst that efficiently converts a carbon-containing stream to $C_2$ to $C_5$ paraffins and methods for using the catalyst for such a conversion. In particular, the present specification relates to hybrid catalysts and methods of using the hybrid catalyst to achieve a high conversion of carbon contained in a synthesis gas feed stream and high stability over time, resulting in a high cumulative productivity of desired products for a given set of operating conditions over a given amount of time. The synthesis gas comprises hydrogen gas and a carbon-containing gas selected from the group consisting of carbon monoxide, carbon dioxide, and mixtures thereof and is converted to desired products while minimizing the conversion of the feed carbon to $CO_2$.

Technical Background

For a number of industrial applications, a desirable starting material is a lower hydrocarbon, including in particular $C_2$ to $C_5$ paraffins that can then be converted to olefins, for use in or as starting materials to produce plastics, fuels, and various downstream chemicals. These $C_2$ to $C_5$ materials may be saturated or unsaturated and therefore may include ethane, ethylene, propane, propylene, butane, butylene, pentane, or pentene. A variety of processes for producing these lower hydrocarbons has been developed, including petroleum cracking and various synthetic processes.

Synthetic processes for converting feed carbon to desired products, such as hydrocarbons, are known. Some of these synthetic processes begin with use of a hybrid catalyst. Different types of catalysts have also been explored, as well as different kinds of feed streams and proportions of feed stream components. However, many of these synthetic processes have low carbon conversion and much of the feed carbon does not get converted and exits the process in the same form as the feed carbon, or the feed carbon is converted to $CO_2$, or these synthetic processes have low stability over time and the catalyst rapidly loses its activity for carbon conversion to desirable products.

Accordingly, a need exists for processes and systems that have a high conversion of feed carbon to desired products, such as, for example, $C_2$ to $C_5$ paraffins in combination with a high stability of the catalyst.

SUMMARY

According to one embodiment, a process for preparing $C_2$ to $C_5$ paraffins comprises: introducing a feed stream comprising hydrogen gas and a carbon-containing gas selected from the group consisting of carbon monoxide, carbon dioxide, and mixtures thereof into a reaction zone of a reactor; and converting the feed stream into a product stream comprising $C_2$ to $C_5$ paraffins in the reaction zone in the presence of a hybrid catalyst. The hybrid catalyst comprising: a metal oxide catalyst component comprising copper, chromium, and zinc; and a microporous catalyst component that is a molecular sieve having eight member ring (8-MR) pore openings. The metal oxide catalyst component satisfies: an atomic ratio of Cu/Zn from 0.01 to 3.00; an atomic ratio of Cr/Zn from 0.01 to 1.50; and an atomic percentage of (Al+Cr) from greater than 0.0 at % to 50.0 at % based on a total amount of metal in the metal oxide catalyst component.

In another embodiment, a hybrid catalyst comprises: a metal oxide catalyst component comprising copper, chromium, and zinc; and a microporous catalyst component that is a molecular sieve having 8-MR pore openings. The metal oxide catalyst component is prepared by: precipitating solids from a solution comprising copper salt, chromium salt, and zinc salt in a solvent to obtain a precipitate comprising copper, chromium, and zinc; and calcining the precipitate at a temperature from 300° C. to 600° C. The metal oxide catalyst component satisfies: an atomic ratio of Cu/Zn from 0.01 to 3.00; an atomic ratio of Cr/Zn from 0.01 to 1.50; and an atomic percentage of (Al+Cr) from greater than 0.0 at % to 50.0 at % based on a total amount of metal in the metal oxide catalyst component.

Additional features and advantages will be set forth in the detailed description which follows, and in part will be readily apparent to those skilled in the art from that description or recognized by practicing the embodiments described herein, including the detailed description which follows and the claims.

It is to be understood that both the foregoing general description and the following detailed description describe various embodiments and are intended to provide an overview or framework for understanding the nature and character of the claimed subject matter.

DETAILED DESCRIPTION

Reference will now be made in detail to embodiments of hybrid catalysts and methods using the hybrid catalyst to prepare $C_2$ to $C_5$ paraffins. In one embodiment, a process for preparing $C_2$ to $C_5$ paraffins comprises: introducing a feed stream comprising hydrogen gas and a carbon-containing gas selected from the group consisting of carbon monoxide, carbon dioxide, and mixtures thereof into a reaction zone of a reactor; and converting the feed stream into a product stream comprising $C_2$ to $C_5$ paraffins in the reaction zone in the presence of a hybrid catalyst. The hybrid catalyst comprising: a metal oxide catalyst component comprising copper, chromium, and zinc; and a microporous catalyst component that is a molecular sieve having 8-MR pore openings. The metal oxide catalyst component satisfies: an atomic ratio of Cu/Zn from 0.01 to 3.00; an atomic ratio of Cr/Zn from 0.01 to 1.50; and an atomic percentage of (Al+Cr) from greater than 0.0 at % to 50.0 at % based on a total amount of metal in the metal oxide catalyst component. In another embodiment, a hybrid catalyst comprises: a metal oxide catalyst component comprising copper, chromium, and zinc; and a microporous catalyst component that is a molecular sieve having 8-MR pore openings. The metal oxide catalyst component is prepared by: precipitating solids from a solution comprising copper salt, chromium salt, and zinc salt in a solvent to obtain a precipitate comprising copper, chromium, and zinc; and calcining the precipitate at a temperature from 300° C. to 600° C. The metal oxide catalyst component satisfies: an atomic ratio of Cu/Zn from 0.01 to 3.00; an atomic ratio of Cr/Zn from 0.01 to 1.50; and an atomic percentage of (Al+Cr) from greater than 0.0 at % to 50.0 at % based on a total amount of metal in the metal oxide catalyst component.

The use of hybrid catalysts to convert feed streams comprising carbon to desired products, such as, for example, $C_2$ to $C_5$ paraffins, is known. However, many known hybrid catalysts are inefficient because they exhibit a low feed carbon conversion and/or deactivate quickly as they are used, leading to a low cumulative $C_2$-$C_5$ hydrocarbon productivity (kg of product/kg of catalyst) for a given set of operating conditions over a given amount of time. In contrast, hybrid catalysts disclosed and described herein combine an improved feed carbon conversion and an improved stability, overall exhibiting an improved cumulative $C_2$-$C_5$ hydrocarbon productivity for the same given set of operating conditions over the same given amount of time. The composition of such hybrid catalysts used in embodiments is discussed below. In summary, hybrid catalysts closely couple sequential reactions on each of the two independent catalysts. In the first step, a feed stream comprising hydrogen gas ($H_2$) and at least one of carbon monoxide (CO), carbon dioxide ($CO_2$), or a mixture of CO and $CO_2$, such as, for example, syngas, is converted into oxygenated hydrocarbons. In the second step, these oxygenates are converted into hydrocarbons (mostly short chain hydrocarbons, such as, for example $C_2$ to $C_5$ paraffins). The continued withdrawal of oxygenates formed in the first step by the reactions of the second step ensure that there is no thermodynamic limit to achieve close to 100% (>99.9%) feed carbon conversion to hydrocarbons.

Hybrid catalyst systems comprise a metal oxide catalyst component, which converts the feed stream to oxygenated hydrocarbons, and a microporous catalyst component (such as, for example a zeolite component), which converts the oxygenates to hydrocarbons. Known hybrid catalyst systems based on copper-zinc-aluminum metal oxide catalyst components show high initial activity but low stability of feed conversion over time while known hybrid catalyst systems based on chromium-zinc metal oxide catalyst components show good stability over time but have low activity. There is therefore a need for a metal oxide catalyst component that results in a high activity as well as a high stability for feed conversion when combined with a microporous catalyst component in a hybrid catalyst process. It should be understood that, as used herein, the "metal oxide catalyst component" includes metals in various oxidation states. In some embodiments, the metal oxide catalyst component may comprise more than one metal oxide and individual metal oxides within the metal oxide catalyst component may have different oxidation states. Thus, the metal oxide catalyst component is not limited to comprising metal oxides with homogenous oxidation states.

Embodiments of hybrid catalysts and systems for using hybrid catalysts disclosed herein comprise a copper, chromium, zinc, and optionally aluminum containing metal oxide catalyst component in combination with a microporous catalyst component, such as, for example, SAPO-34 molecular sieve. The hybrid catalysts disclosed and described herein convert feed streams to short chain paraffins with both high activity as well as high stability of feed conversion over time. The hybrid catalysts disclosed and described herein enable higher stability than is commonly achieved with known copper-zinc-aluminum-oxide based hybrid mixtures and enable higher activity than is commonly achieved with known chromium-zinc-oxide based hybrid mixtures. Thus, by using hybrid catalysts according to embodiments disclosed and described herein, a combination of high activity and high stability is achieved in a hybrid process, leading to a high cumulative $C_2$-$C_5$ hydrocarbon productivity (kg of product/kg of catalyst) for a given set of operating conditions over a given amount of time.

In embodiments, the metal oxide catalyst component, such as, for example, copper-chromium-zinc(-aluminum) metal oxide catalyst component, is prepared by co-precipitation. Alternative synthesis routes show inferior activity and/or stability. For instance, deposition of copper on a highly stable (but less active) chromium-zinc oxide catalyst shows sufficient initial activity, but the catalyst quickly deactivates. Likewise, a metal oxide catalyst component formed from a physical mix of a copper-zinc-aluminum oxide catalyst and a chromium-zinc oxide catalyst has lower stability as compared to the copper-chromium-zinc(-aluminum) catalyst according to embodiments disclosed and described herein. Therefore, embodiments of the hybrid catalyst are made according to the co-precipitation method, which is described in more detail below.

Metal catalyst components for use in a hybrid catalyst according to embodiments will now be described. As referred to above, metals commonly used as constituents of the metal oxide catalyst component of a hybrid catalyst include combinations of zinc (Zn), chromium (Cr), and copper (Cu). In addition, Aluminum (Al) may optionally be included. However, not all combinations of these metals result in a metal oxide catalyst component that can be used in a hybrid catalyst having good activity and good stability. Unexpectedly, it was found that there is a relatively narrow compositional range of atomic ratios of these metals that can be used in the metal oxide catalyst component of a hybrid catalyst that yields good activity and good stability. It was further unexpectedly found that the method used to form the metal oxide catalyst component has a distinct effect on the performance of the hybrid catalyst. For instance, hybrid catalysts where the metal oxide catalyst component is formed by a co-precipitation method have better activity and/or stability than hybrid catalysts where the metal oxide catalyst component is formed by other methods, such as physical mixing or impregnation.

In embodiments disclosed herein, the composition of the metal oxide catalyst component is designated by an atomic percentage of its various metal constituents (i.e., Zn, Cu, Cr, and optionally Al) based on the total amount of metals present in the metal oxide catalyst component (i.e., the sum of all metals in the metal oxide catalyst component equals 100%). In one or more embodiments, the composition of the metal oxide catalyst component is designated by atomic ratios of Cu/Zn and Cr/Zn as well as the sum (in atomic percent) of Al and Cr (Al+Cr). Thus, 50% Cu means that Cu comprises 50% of all metal atoms present in the metal oxide catalyst component. And an atomic ratio of Cu/Zn means a ratio of Cu atoms to Zn atoms. As a non-limiting example, 25% Cu and 25% Zn would mean that Cu comprises 25% of all metal atoms present in the metal oxide catalyst component, Zn comprises 25% of all metal atoms present in the metal oxide catalyst component, a sum of Cu and Zn is 50% of all metal atoms present in the metal oxide catalyst component, and a ratio of Cu/Zn is 1.00 (25%/25%).

A ratio of Cu/Zn is, in one or more embodiments, from 0.01 to 3.00, such as from 0.01 to 2.75, from 0.01 to 2.50, from 0.01 to 2.25, from 0.01 to 2.00, from 0.01 to 1.75, from 0.01 to 1.50, from 0.01 to 1.25, from 0.01 to 1.00, from 0.01 to 0.75, or from 0.01 to 0.50. In other embodiments, a ratio of Cu/Zn is from 0.25 to 2.50, such as from 0.25 to 2.25, from 0.25 to 2.00, from 0.25 to 1.75, from 0.25 to 1.50, from 0.25 to 1.25, or from 0.25 to 1.00. In yet other embodiments, a ratio of Cu/Zn is from 0.01 to 2.00, from 0.01 to 1.50, from 0.25 to 1.00, or from 0.30 to 0.80. When the ratio of Cu/Zn becomes too large, the activity and/or stability of the hybrid catalyst decreases, leading to a lower cumulative $C_2$ to $C_5$ productivity.

In other embodiments a ratio of Cr/Zn is from 0.01 to 1.50, such as from 0.01 to 1.25, from 0.01 to 1.00, from 0.01 to 0.75, or from 0.01 to 0.50. In other embodiments, a ratio of Cr/Zn is from 0.20 to 1.50, from 0.20 to 1.25, from 0.20 to 1.00, or from 0.20 to 0.75. In yet other embodiments, a ratio of Cr/Zn is from 0.01 to 1.25, from 0.01 to 1.00, or from 0.20 to 0.50. When the ratio of Cr/Zn becomes too large, the activity and/or stability of the hybrid catalyst decreases, leading to a lower cumulative $C_2$ to $C_5$ productivity.

In one or more embodiments, a sum of the atomic percentage of Al+Cr based on the total metal content of the metal oxide catalyst is from greater than 0.0% to 50.0%, such as from greater than 0.0% to 45.0%, or from greater than 0.0% to 40.0%, from greater than 0.0% to 35.0%, from greater than 0.0% to 30.0%, from greater than 0.0% to 25.0%, or from greater than 0.0% to 20.0%. In other embodiments, a sum of the atomic percentage of Al+Cr based on the total metal content of the metal oxide catalyst is from 10.0% to 50.0%, such as from 10.0% to 45.0%, or from 10.0% to 40.0%, from 10.0% to 35.0%, from 10.0% to 30.0%, from 10.0% to 25.0%, or from 10.0% to 20.0%. When the sum of the atomic percentage of Al+Cr becomes too large, the activity and/or stability of the hybrid catalyst decreases, leading to a lower cumulative $C_2$ to $C_5$ productivity.

As referred to hereinabove, in embodiments disclosed and described herein, the metal oxide catalyst component of the hybrid catalyst is formed by a co-precipitation method. This co-precipitation method allows for the metal oxide constituents of the metal oxide catalyst components to be more homogeneously incorporated with one another than if the metal oxide catalyst component was formed by some other method, such as, for example, physical mixing or impregnation. Thus, forming a metal oxide catalyst component by the co-precipitation method leads to a metal oxide catalyst component that has a different structure than the structure that is achieved by making the metal oxide catalyst component by other methods, and hybrid catalysts that comprise a metal oxide catalyst component that is made by the co-precipitation method have higher activity and/or stability as compared to hybrid catalysts that comprise a metal oxide catalyst component that is made by other methods.

According to one or more embodiments, a metal oxide catalyst component may be made by forming an aqueous mixture of Cu-, Cr-, Zn-, and optionally Al-containing components. For example, in some embodiments, the Cu-, Cr-, Zn-, and optionally Al-containing components may be nitrates, such as copper nitrate ($Cu(NO_3)_2$), chromium nitrate ($Cr(NO_3)_3$), zinc nitrate ($Zn(NO_3)_2$), and optionally aluminum nitrate ($Al(NO_3)_3$). In other embodiments, the Cu-, Cr-, Zn-, and optionally Al-containing components used to prepare the catalyst may include any commonly known counterions such as, for example, acetates, formates, and the like, provided that the selected counterions decompose or combust at the calcination temperature to form oxides without leaving undesired residues. It should be understood that the amount of the Cu-, Cr-, Zn-, and optionally Al-containing components are selected such that the resulting metal oxide catalyst component will have values of the Cu/Zn ratio, the Cr/Zn ratio, and the sum of Cr+Al as defined and recited above. The Cu-, Cr-, Zn-, and optionally Al-containing components are, in embodiments, added to water to form an aqueous mixture of the Cu-, Cr-, Zn-, and optionally Al-containing components.

In embodiments, a precipitating agent is prepared to be used to precipitate the Cu-, Cr-, Zn-, and optionally Al-containing components from the above-referenced aqueous mixture. The precipitating agent, in one or more embodiments, is an aqueous mixture of a carbonate and/or hydroxide, such as, for example, ammonium carbonate (($NH_4)_2CO_3$), sodium carbonate ($Na_2CO_3$), sodium hydroxide (NaOH) or mixtures thereof. It should be understood that in embodiments other conventional precipitating agents may be used.

After the aqueous mixture of Cu-, Cr-, Zn-, and optionally Al-containing components and the precipitating agent are formulated, a precipitate is formed by adding these components to water maintained at a temperature from 40° C. to 80° C., such as from 45° C. to 75° C., from 50° C. to 70° C., from 55° C. to 65° C., or about 60° C. while mixing. In some embodiments, the aqueous mixture of Cu-, Cr-, Zn-, and optionally Al-containing components and the precipitating agent are slowly added to the water so as to improve mixing of the components. The combination of the aqueous mixture of Cu-, Cr-, Zn-, and optionally Al-containing components and the precipitating agent is maintained at a pH from 6.0 to 9.0, such as from 6.5 to 7.5, or from 7.0 to 7.5. The pH may be controlled by adjusting the ratio of the aqueous mixture of Cu-, Cr-, Zn-, and optionally Al-containing components and precipitating agent that is added to the precipitating combination. This ratio may be adjusted by controlling the rate at which each component is added to the mixture. In some embodiments, the precipitate is aged in the mother liquor for a duration from 0.5 hours to 6.0 hours, such as from 1.0 hour to 5.0 hours, from 1.5 hours to 4.5 hours, from 2.0 hours to 4.0 hours, or from 2.5 hours to 3.5 hours.

The precipitate may be collected by conventional filtering, washing, and drying methods, or by other methods known to one of ordinary skill in the art. Once collected, the precipitate is calcined to form the metal oxide catalyst component that is used in a hybrid catalyst according to embodiments disclosed and described herein. The calcining process includes heating the precipitate to a temperature from 300 degrees Celsius (° C.) to 600° C., such as from 375° C. to 575° C., from 400° C. to 550° C., from 425° C. to 525° C., from 250° C. to 500° C., or about 400° C. The duration of the calcining process may, in embodiments, be greater than or equal to 0.50 hours, such as greater than 1.00 hours, greater than 1.50 hours, greater than 2.00 hours, greater than 2.50 hours, greater than 3.00 hours, greater than 3.50 hours, greater than 4.00 hours, greater than 4.50 hours, or greater than 5.00 hours. In other embodiments, the duration of the calcining process may be from 0.50 hours to 8.00 hours, such as from 1.00 hours to 7.50 hours, from 1.50 hours to 7.00 hours, from 2.00 hours to 6.50 hours, from 2.50 hours to 6.00 hours, from 3.00 hours to 5.50 hours, from 3.50 hours to 5.00 hours, or from 4.00 hours to 4.50 hours.

In one or more embodiments, after the precipitate has been calcined to form the metal oxide catalyst, it is physically mixed with a microporous catalyst component. The microporous catalyst component is, in embodiments, selected from molecular sieves having 8-MR pore openings and having a framework type selected from the group consisting of the following framework types CHA, AEI, AFX, ERI, LTA, UFI, RTH, and combinations thereof, the framework types corresponding to the naming convention of the International Zeolite Association. It should be understood that in embodiments, both aluminosilicate and silicoaluminophosphate frameworks may be used. In certain embodiments, the microporous catalyst component may be SAPO-34 silicoaluminophosphate having a Chabazite (CHA) framework type. Examples of these may include, but are not necessarily limited to: CHA embodiments selected from SAPO-34 and SSZ-13; and AEI embodiments such as SAPO-18. Combinations of microporous catalyst components having any of the above framework types may also be employed. It should be understood that the microporous catalyst component may have different membered ring pore opening depending on the desired product. For instance, microporous catalyst component having 8-MR to 12-MR pore openings could be used depending on the desired product. However, to produce $C_2$ to $C_5$ paraffins, a microporous catalyst component having 8-MR pore openings is used in embodiments.

The metal oxide catalyst component and the microporous catalyst component of the hybrid catalyst may be mixed together by any suitable means, such as, for example, physical mixing—such as shaking, stirring, or other agitation. The metal oxide catalyst component and the microporous catalyst component may be present in the reaction zone, typically as a hybrid catalyst in a catalyst bed, in a weight/weight (wt/wt) ratio (metal oxide catalyst component:microporous catalyst component) ranging from 0.1:1 to 10:1, such as from 0.5:1 to 9:1.

After the metal oxide catalyst component has been formed by a co-precipitation/calcination method and combined with a microporous catalyst component to form a hybrid catalyst, the hybrid catalyst may be used in methods for converting carbon in a carbon-containing feed stream to $C_2$ to $C_5$ paraffins. Such processes will be described in more detail below.

In embodiments, the metal oxide catalyst component may be reduced within the reactor prior to exposure to the feed stream by exposing the metal oxide catalyst component to conventional reducing gases. In other embodiments, the metal oxide catalyst component may be reduced within the reactor upon exposure to reducing gases in the feed stream such as hydrogen and carbon monoxide.

According to embodiments, a feed stream is fed into a reaction zone, the feed stream comprising hydrogen ($H_2$) gas and a carbon-containing gas selected from carbon monoxide (CO), carbon dioxide ($CO_2$), and combinations thereof. In some embodiments, the $H_2$ gas is present in the feed stream in an amount of from 10 volume percent (vol %) to 90 vol %, based on combined volumes of the $H_2$ gas and the gas selected from CO, $CO_2$, and combinations thereof. In some embodiments $H_2$ is present in the feed stream in an amount from 20 vol % to 80 vol %, such as from 30 vol % to 70 vol %, or 40 vol % to 60 vol %. The feed stream is contacted with a hybrid catalyst in the reaction zone. The hybrid catalyst comprises a metal oxide catalyst component and a microporous catalyst component. In some embodiments, the metal oxide catalyst component of the hybrid catalyst is a metal oxide catalyst component formed by the co-precipitation method described above. In certain embodiments, the microporous catalyst component is SAPO-34.

As referenced above, in embodiments, the feed stream comprises $H_2$ and a carbon-containing gas stream selected from CO, $CO_2$, and a combination of CO and $CO_2$. In embodiments where the feed stream comprises $H_2$ and a combination of CO and $CO_2$, the ratio of $CO_2$ to CO in the feed stream is from 0.1:1.0 to 0.7:1.0, such as from 0.3:1.0 to 0.6:1.0, or from 0.4:1 to 0.5:1.0. If the ratio of $CO_2$ to CO in the feed stream is too high, such as above 0.7:1.0, the cumulative amount of desired product produced for a given set of operating conditions over a given amount of time may be reduced. However, it can be difficult and costly to remove enough $CO_2$ from a feed stream to get the ratio of $CO_2$ to CO below 0.1:1.0.

It should be understood that the effectiveness of the hybrid catalyst will be higher for feed streams containing CO as the carbon-containing gas, and that the effectiveness of the hybrid catalyst decreases as a smaller portion of the carbon-containing gas in the feed stream is CO. However, that is not to say that the hybrid catalyst disclosed and described herein cannot be used in methods where the feed stream comprises $CO_2$ as all, or a large portion, of the carbon-containing gas.

The feed stream is contacted with the hybrid catalyst in the reaction zone under reaction conditions sufficient to form a product stream comprising $C_2$ to $C_5$ paraffins. The reaction conditions comprise a temperature within reaction zone ranging, according to one or more embodiments, from 300° C. to 500° C., such as from 300° C. to 475° C., from 300° C. to 450° C., from 300° C. to 425° C., from 300° C. to 400° C., from 300° C. to 375° C., from 300° C. to 350° C., or from 300° C. to 325° C. In other embodiments, the temperature within the reaction zone is from 325° C. to 500° C., from 350° C. to 500° C., from 375° C. to 500° C., from 400° C. to 500° C., from 425° C. to 500° C., from 450° C. to 500° C., or from 475° C. to 500° C. In yet other embodiments, the temperature within the reaction zone is from 300° C. to 500° C., such as from 325° C. to 475° C., from 350° C. to 450° C., or from 375° C. to 425° C.

The reaction conditions also, in embodiments, include a pressure inside the reaction zone of at least 20 bar (2,000 kPa), such as at least 30 bar (3,000 kPa), at least 40 bar (4,000 kPa), or at least 50 bar (5,000 kPa). In other embodiments, the reaction conditions include a pressure inside the reaction zone from 20 bar (2,000 kilopascals (kPa)) to 70 bar (7,000 kPa), such as from 20 bar (2,000 kPa) to 65 bar (6,500 kPa), from 20 bar (2,000 kPa) to 60 bar (6,000 kPa), from 20 bar (2,000 kPa) to 55 bar (5,500 kPa), from 20 bar (2,000 kPa) to 50 bar (5,000 kPa), from 20 bar (2,000 kPa) to 45 bar (4,500 kPa), from 20 bar (2,000 kPa) to 40 bar (4,000 kPa), from 20 bar (2,000 kPa) to 35 bar (3,500 kPa), from 20 bar (2,000 kPa) to 30 bar (3,000 kPa), or from 20 bar (2,000 kPa) to 25 bar (2,500 kPa). In other embodiments, a pressure inside the reaction zone is from 25 bar (2,500 kPa) to 70 bar (7,000 kPa), such as from 30 bar (3,000 kPa) to 70 bar (7,000 kPa), from 35 bar (3,500 kPa) to 70 bar (7,000 kPa), from 40 bar (4,000 kPa) to 70 bar (7,000 kPa), from 45 bar (4,500 kPa) to 70 bar (7,000 kPa), from 50 bar (5,000 kPa) to 70 bar (7,000 kPa), from 55 bar (5,500 kPa) to 70 bar (7,000 kPa), from 60 bar (6,000 kPa) to 70 bar (7,000 kPa), or from 65 bar (6,500 kPa) to 70 bar (7,000 kPa). In still other embodiments a pressure inside the reaction zone is from 25 bar (2,500 kPa) to 65 bar (6,500 kPa), such as from 30 bar (3,000 kPa) to 60 bar (6,000 kPa), from 35 bar (3,500 kPa) to 55 bar (5,500 kPa), from 40 bar (4,000 kPa) to 50 bar (5,000 kPa), or about 50 bar (5,000 kPa).

The above process has utility in that it converts a feed stream that comprises, consists essentially of, or consists of $H_2$ gas and a carbon-containing gas selected from CO, $CO_2$, or a combination thereof, to a product stream that comprises a combination of $C_2$ to $C_5$ paraffins. The product stream itself has utility as a cracker feed stream to produce certain olefins and/or as a starting material or intermediate to produce a range of chemical products including plastics, fuels and the like.

As mentioned above, the combined activity and stability of the hybrid catalysts disclosed and described herein is greater than the combined activity and stability of the heretofore known hybrid catalysts. This combination of activity and stability leads to a greater cumulative productivity of desired products compared to the heretofore known hybrid catalysts. The cumulative productivity is a measurement of the cumulative mass of desired product produced per unit mass of catalyst for a given set of operating conditions over a given amount of time. This measure essentially combines the feed conversion, stability, selectivity and productivity of a catalyst, hereby providing a simple method to compare different catalysts through a single performance indicator. For the catalysts disclosed and described herein, the cumulative $C_2$-$C_5$ hydrocarbon productivity is defined by the following equation and the specified testing protocol, the combination of which is also referred to as "the hydrocarbon productivity protocol":

$$\int_0^{120} \sum_{i=2}^{5} \frac{(N_i * MM_i + N_i^= * MM_i^=)}{W} dt$$

| TOS t (h) | 0-48 h | 48-72 h | 72 h-96 h | 96 h-120 h |
|---|---|---|---|---|
| Temperature (° C.) | 400 | 400 | 400 | 400 |
| Pressure (bar) | 50 | 50 | 50 | 50 |
| H$_2$/CO | 3 | 3 | 3 | 3 |
| Duration (h) | 48 | 24 | 24 | 24 |
| Feed Flow (ml/min)[b] | CO: 15 ml/min H$_2$: 45 ml/min He: 5 ml/min | CO: 30 ml/min H$_2$: 90 ml/min He: 10 ml/min | CO: 60 ml/min H$_2$: 180 ml/min He: 10 ml/min | CO: 15 ml/min H$_2$: 45 ml/min He: 5 ml/min |
| Catalyst Loading[a] | | 1 g | | |

[a]The catalyst is a physical mixture of the metal oxide component and the molecular sieve in a 1/3 mass ratio.
[b]Volumetric flow rates in mL/min refer to standard cubic centimeters of gas, which is the ideal gas volume at 25° C. and 1 atmosphere of pressure.

with $N_i$ and $N_i^=$ defined as the molar outlet flow in mol/h of respectively paraffins and olefins with carbon number i. $MM_i$ and $MM_i^=$ are defined as the molar mass of respectively paraffins and olefins with carbon number i in kg/mol. W is defined as the weight of the hybrid catalyst in kg and the time on stream t is specified in hours.

In one or more embodiments, the cumulative productivity, as defined above, of the hybrid catalyst may be measured by a ratio of kilograms of $C_2$ to $C_5$ hydrocarbons produced to kilogram of catalyst (kg/kg cat) at the end of the 120 hour test above. The productivity of the hybrid catalyst is, in embodiments, greater than or equal to 31.3 kg/kg cat, such as greater than or equal to 32.0 kg/kg cat, greater than or equal to 34.0 kg/kg cat, greater than or equal to 36.0 kg/kg cat, greater than or equal to 38.0 kg/kg cat, greater than or equal to 40.0 kg/kg cat, greater than or equal to 42.0 kg/kg cat, greater than or equal to 44.0 kg/kg cat, greater than or equal to 46.0 kg/kg cat, greater than or equal to 48.0 kg/kg cat, greater than or equal to 50.0 kg/kg cat, or greater than or equal to 52.0 kg/kg cat. In other embodiments, the productivity of the hybrid catalyst is from 31.3 kg/kg cat to 60.0 kg/kg cat, such as from 32.0 kg/kg cat to 60.0 kg/kg cat, from 34.0 kg/kg cat to 60.0 kg/kg cat, from 36.0 kg/kg cat to 60.0 kg/kg cat, from 38.0 kg/kg cat to 60.0 kg/kg cat, from 40.0 kg/kg cat to 60.0 kg/kg cat, from 42.0 kg/kg cat to 60.0 kg/kg cat, from 44.0 kg/kg cat to 60.0 kg/kg cat, from 46.0 kg/kg cat to 60.0 kg/kg cat, from 48.0 kg/kg cat to 60.0 kg/kg cat, form 50.0 kg/kg cat to 60.0 kg/kg cat, or from 52.0 kg/kg cat to 60.0 kg/kg cat.

EXAMPLES

Embodiments will be further clarified by the following examples.

Inventive Examples 1-23 and Comparative Examples 1-35

Various copper-chromium-zinc(-aluminum) catalysts were prepared by following the co-precipitation method. Appropriate quantities (see Table 1) of Cu(NO$_3$)$_2$.3H$_2$O, Cr(NO$_3$)$_3$.9H$_2$O, Zn(NO$_3$)$_2$.6H$_2$O and Al(NO$_3$)$_3$.9H2O were added to distilled water (H$_2$O), targeting a total metal concentration of 1 mol/L. In addition, a 2 M solution of (NH$_4$)$_2$CO$_3$ or 1 M solution of Na$_2$CO$_3$ was prepared as a precipitating agent. The metal nitrate and precipitating agent solutions were simultaneously added dropwise to a stirred beaker of distilled H$_2$O and maintained at a pH of about 7 and a temperature of about 50° C. Co-precipitated materials were filtered, washed with distilled water, dried overnight in static air at 85° C., and subsequently calcined at 400° C. for 2 h.

For the catalytic tests, 0.25 gram of copper-chromium-zinc(-aluminum) catalyst was physically mixed with 0.75 gram of a silicoaluminophosphate catalyst (SAPO-34) by gently shaking them together in a bottle. Each of the catalysts had a particle size before mixing within a range of from 40 mesh (0.422 millimeter) to 80 mesh (0.178 millimeter). Prior to contacting with syngas, the catalyst was reduced at 300° C. and at atmospheric pressure for 6 hours by flowing 100 ml/min H$_2$. The catalytic performance test was carried out at 50 bar (5.0 MPa), 400° C. at different subsequent flow conditions as shown in Table 1 below.

TABLE 1

| TOS t (h) | Condition 1 0-48 h | Condition 2 48-72 h | Condition 3 72 h-96 h | Condition 4 96 h-120 h |
|---|---|---|---|---|
| Temperature (° C.) | 400 | 400 | 400 | 400 |
| Pressure (bar) | 50 | 50 | 50 | 50 |
| h$_2$/co | 3 | 3 | 3 | 3 |
| Duration (h) | 48 | 24 | 24 | 24 |
| Flow (ml/min) | CO: 15 ml/min H$_2$: 45 ml/min He: 5 ml/min | CO: 30 ml/min H$_2$: 90 ml/min He: 10 ml/min | CO: 60 ml/min H$_2$: 180 ml/min He: 10 ml/min | CO: 15 ml/min H$_2$: 45 ml/min He: 5 ml/min |

The experimental compositions of exemplary catalyst and their performance are shown in Table 2 below, and the experimental compositions of comparative catalysts and their performance are shown in Table 3 below. The performance of the catalysts was measured by the cumulative productivity of $C_2$ to $C_5$ hydrocarbons over the complete catalytic test.

TABLE 2

| Ex. | Copper Nitrate (g) | Zinc Nitrate (g) | Aluminum Nitrate (g) | Chromium Nitrate (g) | PA carbonate | Cu XRF (at %) | Zn XRF (at %) | Al XRF (at %) | Cr XRF (at %) | Cumulative Productivity $C_2$-$C_5$ hydrocarbons (kg/kg Cat) |
|---|---|---|---|---|---|---|---|---|---|---|
| 1 | 6.07 | 14.62 | 3.27 | 5.27 | $NH_4$ [2M] | 12.1% | 51.5% | 13.6% | 22.9% | 38.7 |
| 2 | 9.28 | 12.10 | 0.00 | 8.38 | Na [1M] | 39.4% | 40.4% | 0.0% | 20.3% | 42.1 |
| 3 | 2.41 | 16.46 | 0.00 | 13.88 | Na [1M] | 10.4% | 55.4% | 0.0% | 34.2% | 34.9 |
| 4 | 7.12 | 11.64 | 8.14 | 3.88 | Na [1M] | 31.9% | 40.5% | 18.1% | 9.6% | 47.5 |
| 5 | 8.45 | 13.11 | 0.00 | 8.38 | $NH_4$ [2M] | 19.6% | 49.9% | 0.0% | 30.5% | 43.2 |
| 6 | 2.26 | 17.97 | 7.67 | 3.92 | $NH_4$ [2M] | 2.6% | 50.6% | 30.3% | 16.5% | 33.0 |
| 7 | 3.84 | 13.26 | 0.00 | 15.83 | Na [1M] | 16.5% | 44.2% | 0.0% | 39.3% | 39.2 |
| 8 | 8.01 | 13.65 | 0.00 | 8.39 | $NH_4$ [2M] | 20.6% | 52.5% | 0.0% | 26.9% | 49.5 |
| 9 | 7.62 | 12.98 | 5.57 | 3.99 | Na [1M] | 33.1% | 44.4% | 12.9% | 9.6% | 47.0 |
| 10 | 5.99 | 12.03 | 5.94 | 7.59 | $NH_4$ [2M] | 12.6% | 40.4% | 20.3% | 26.7% | 44.5 |
| 11 | 8.07 | 8.33 | 0.00 | 15.44 | $NH_4$ [2M] | 22.9% | 32.2% | 0.0% | 44.9% | 36.1 |
| 12 | 8.52 | 11.88 | 5.57 | 3.99 | Na [1M] | 37.0% | 40.7% | 12.5% | 9.8% | 52.3 |
| 13 | 2.31 | 19.48 | 5.60 | 4.01 | Na [1M] | 10.9% | 66.4% | 12.0% | 10.7% | 35.6 |
| 14 | 11.31 | 8.47 | 5.55 | 3.98 | $NH_4$ [2M] | 28.7% | 38.3% | 18.2% | 14.8% | 39.1 |
| 15 | 3.40 | 11.12 | 8.07 | 10.82 | Na [1M] | 15.6% | 36.6% | 18.9% | 28.9% | 34.2 |
| 16 | 7.30 | 12.05 | 0.00 | 11.73 | Na [1M] | 31.4% | 39.0% | 0.0% | 29.6% | 39.8 |
| 17 | 3.11 | 15.81 | 8.15 | 4.91 | Na [1M] | 14.2% | 56.3% | 17.3% | 12.2% | 43.7 |
| 18 | 2.42 | 18.03 | 0.00 | 11.76 | $NH_4$ [2M] | 6.9% | 61.2% | 0.0% | 32.0% | 40.2 |
| 19 | 2.43 | 20.49 | 0.00 | 8.43 | Na [1M] | 10.7% | 68.7% | 0.0% | 20.6% | 33.3 |
| 20 | 2.38 | 11.92 | 0.00 | 20.03 | $NH_4$ [2M] | 9.1% | 40.5% | 0.0% | 50.4% | 31.5 |
| 21 | 13.65 | 5.52 | 2.28 | 7.55 | Na [1M] | 59.2% | 19.1% | 3.7% | 18.0% | 36.6 |
| 22 | 11.17 | 7.01 | 3.38 | 8.48 | Na [1M] | 53.4% | 24.2% | 4.3% | 18.1% | 38.9 |
| 23 | 11.68 | 9.47 | 1.44 | 6.40 | Na [1M] | 50.1% | 31.9% | 2.8% | 15.2% | 43.7 |

TABLE 3

| C. Ex. | Copper Nitrate (g) | Zinc Nitrate (g) | Aluminum Nitrate | Chromium Nitrate (g) | PA carbonate | Cu XRF (at %) | Zn XRF (at %) | Al XRF (at %) | Cr XRF (at %) | Cumulative Productivity $C_2$-$C_5$ hydrocarbons (kg/kg Cat) |
|---|---|---|---|---|---|---|---|---|---|---|
| 1 | 2.30 | 11.50 | 4.17 | 16.29 | $NH_4$ [2M] | 6.2% | 36.3% | 11.6% | 45.9% | 26.6 |
| 2 | 5.01 | 13.37 | 8.14 | 5.05 | $NH_4$ [2M] | 4.7% | 29.0% | 41.0% | 25.4% | 11.2 |
| 3 | 16.79 | 2.89 | 0.00 | 8.32 | Na [1M] | 69.5% | 10.0% | 0.0% | 20.5% | 20.3 |
| 4 | 12.06 | 2.86 | 0.00 | 16.20 | $NH_4$ [2M] | 38.3% | 11.7% | 0.0% | 50.0% | 22.6 |
| 5 | 8.41 | 5.69 | 4.96 | 13.14 | Na [1M] | 36.6% | 19.5% | 11.4% | 32.5% | 26.8 |
| 6 | 2.19 | 5.26 | 7.94 | 20.85 | Na [1M] | 9.8% | 18.7% | 19.0% | 52.6% | 2.6 |
| 7 | 16.19 | 3.63 | 0.00 | 8.32 | $NH_4$ [2M] | 36.4% | 21.3% | 0.0% | 42.3% | 23.5 |
| 8 | 16.19 | 3.63 | 0.00 | 8.32 | $NH_4$ [2M] | 41.2% | 20.4% | 0.0% | 38.1% | 28.3 |
| 9 | 12.48 | 2.86 | 0.00 | 15.50 | Na [1M] | 51.8% | 9.8% | 0.0% | 38.4% | 23.8 |
| 10 | 12.48 | 2.86 | 0.00 | 15.50 | Na [1M] | 52.3% | 9.4% | 0.0% | 38.2% | 14.4 |
| 11 | 13.31 | 2.67 | 8.06 | 5.78 | $NH_4$ [2M] | 14.6% | 8.5% | 44.4% | 32.6% | 6.7 |
| 12 | 13.31 | 2.67 | 8.06 | 5.78 | $NH_4$ [2M] | 26.1% | 13.2% | 36.4% | 24.2% | 1.7 |
| 13 | 13.09 | 4.35 | 8.09 | 3.86 | Na [1M] | 56.8% | 14.5% | 19.0% | 9.7% | 23.2 |
| 14 | 13.09 | 4.35 | 8.09 | 3.86 | Na [1M] | 55.4% | 14.5% | 20.6% | 9.5% | 22.2 |
| 15 | 15.98 | 2.75 | 5.53 | 3.96 | Na [1M] | 70.8% | 9.4% | 10.2% | 9.6% | 20.2 |
| 16 | 3.66 | 4.99 | 7.96 | 18.75 | $NH_4$ [2M] | 13.6% | 16.9% | 21.5% | 48.0% | 1.5 |
| 17 | 3.23 | 4.59 | 0.00 | 28.50 | $NH_4$ [2M] | 12.9% | 15.5% | 0.0% | 71.6% | 10.0 |
| 18 | 2.60 | 5.35 | 0.00 | 28.51 | Na [1M] | 11.1% | 18.0% | 0.0% | 70.9% | 1.5 |
| 19 | 12.53 | 3.86 | 8.07 | 5.46 | Na [1M] | 54.1% | 13.3% | 19.1% | 13.5% | 31.0 |
| 20 | 13.55 | 3.78 | 8.09 | 3.86 | $NH_4$ [2M] | 15.2% | 15.1% | 46.9% | 22.8% | 10.3 |
| 21 | 15.74 | 4.18 | 0.00 | 8.33 | $NH_4$ [2M] | 37.5% | 23.6% | 0.0% | 38.9% | 23.8 |
| 22 | 6.07 | 2.83 | 0.00 | 26.16 | Na [1M] | 25.7% | 9.7% | 0.0% | 64.6% | 3.0 |
| 23 | 15.98 | 2.75 | 5.53 | 3.96 | $NH_4$ [2M] | 32.8% | 15.4% | 30.1% | 21.8% | 26.2 |
| 24 | 2.36 | 5.65 | 0.00 | 28.52 | $NH_4$ [2M] | 9.3% | 19.2% | 0.0% | 71.6% | 11.9 |
| 25 | 7.96 | 2.64 | 7.98 | 14.76 | $NH_4$ [2M] | 22.2% | 10.2% | 23.8% | 43.9% | 17.1 |
| 26 | 8.83 | 6.16 | 0.00 | 17.10 | Na [1M] | 37.4% | 21.2% | 0.0% | 41.4% | 17.1 |
| 27 | 4.46 | 2.68 | 5.67 | 22.99 | $NH_4$ [2M] | 15.3% | 9.5% | 14.7% | 60.5% | 16.7 |
| 28 | 7.37 | 2.64 | 7.97 | 15.76 | Na [1M] | 32.8% | 9.6% | 17.6% | 40.0% | 24.0 |
| 29 | 3.05 | 7.56 | 8.00 | 16.26 | Na [1M] | 13.6% | 26.7% | 18.9% | 40.9% | 21.3 |
| 30 | 2.22 | 11.08 | 8.05 | 12.85 | $NH_4$ [2M] | 6.2% | 34.3% | 22.6% | 36.9% | 28.0 |
| 31 | 2.28 | 10.56 | 4.96 | 16.75 | Na [1M] | 10.1% | 36.9% | 11.4% | 41.6% | 29.7 |
| 32 | 0.00 | 21.31 | 0.00 | 11.35 | $NH_4$ [2M] | 0.0% | 69.6% | 0.0% | 30.4% | 30.3 |
| 33 | 6.95 | 16.74 | 5.61 | 0.00 | Na [1M] | 30.2% | 56.4% | 13.4% | 0.0% | 14.8 |
| 34 | 0.00 | 14.87 | 0.00 | 20.01 | $NH_4$ [2M] | 0.0% | 50.1% | 0.0% | 49.9% | 31.3 |
| 35 | HiFUEL ® R120 (Alfa Aesar) - Cu: 51 wt %, Zn: 20 wt %, and Al: 5 wt % | | | | | | | | | 26.0 |

From the obtained cumulative $C_2$ to $C_5$ paraffin productivity, it can be observed that all examples 1-23 exhibit a productivity larger than 31.3 kg product/kg catalyst obtained at the testing protocol specified above in Table 1. This lower boundary is the maximum productivity attainable for chromium-zinc based catalysts in this specific catalytic test protocol (Comparative Example 34). Based on the different catalyst compositions and the threshold cumulative productivity of 31.3 kg/kg Cat, the optimized range of the CuCrZnAl catalysts can be summarized as the combination of the following three compositional descriptors:

0<Cu/Zn≤3;
0<Cr/Zn≤1.5; and
0.0 at %<Al+Cr≤50.0 at %.

As can be observed from Examples 8 and 9, the addition of aluminum to the copper-chromium-zinc catalyst can be considered optional, as comparable performance can be obtained for catalyst compositions with and without aluminum.

Example 24

A copper-chromium-zinc-aluminum catalyst was prepared by following the co-precipitation method. A metal oxide catalyst component was prepared by adding 6.07 grams (g) of $Cu(NO_3)_2 \cdot 3H_2O$, 5.28 g of $Cr(NO_3)_3 \cdot 9H_2O$, 14.65 g of $Zn(NO_3)_2 \cdot 6H_2O$ and 3.27 g of $Al(NO_3)_3 \cdot 9H_2O$ to distilled water ($H_2O$), targeting a total metal concentration of 1 mol/L. In addition, a 0.5 M solution of $(NH_4)_2CO_3$ was prepared as a precipitating agent. The metal nitrate and precipitating agent solutions were simultaneously added dropwise to a stirred beaker containing 200 mL distilled $H_2O$ maintained at pH of about 7 and temperature of about 70° C., where the metal oxide catalyst precursor components co-precipitated out of the solution. The co-precipitated materials were filtered, washed with distilled water, dried in static air at 85° C. overnight, and subsequently calcined at 400° C. for 2 hours (h). The final catalyst had Cu, Cr, Zn and Al contents of 12.5, 16.8, 61.9 and 8.8 atomic % based on the total metal content in the catalyst, respectively.

For a catalytic test, 1 gram of copper-chromium-zinc-aluminum catalyst was physically mixed with 0.5 gram of a silicoaluminophosphate catalyst (SAPO-34) by gently shaking them together in a bottle to form a hybrid catalyst. Each of the catalysts had a particle size before mixing within a range of from 40 mesh (0.422 millimeter (mm)) to 80 mesh (0.178 mm). Prior to contacting the hybrid catalyst with syngas in a heated reactor tube with an internal diameter of 0.5 inches. The hybrid catalyst was reduced at 270° C. at 10 bar for 6 hours by flowing 100 ml/min $H_2$. A catalytic performance test was carried out at 50 bar (5.0 MPa), 400° C. by flowing 22.5 ml/min CO, 67.5 ml/min $H_2$ and 10 ml/min He over the catalyst. The results are shown in Table 4 below. The reactor effluent composition was obtained by gas chromatography and the conversion and selectivities were calculated using the following equations:

CO Conversion=$X_{CO}$(%)=[($n_{CO, in}-n_{CO, out}$)/$n_{CO, in}$]·100; and

Selectivity of product $j=S_j$(%)=[$\alpha_j \cdot n_{j, out}$/($n_{CO, in}-n_{CO, out}$)]·100, where α is the number of carbon atoms for product j, $n_{j, out}$ is the molar outlet of product j.

TABLE 4

|  | 23 hrs on stream | 145 hrs on stream |
|---|---|---|
| Conversion [%] CO | 80 | 80 |
| Selectivity $C_1$ | 4.2 | 5.9 |
| $C_2$ | 17.0 | 15.5 |
| $C_3$ | 29.3 | 29.3 |
| $C_4$ | 8.5 | 9.0 |
| $C_5$ and higher | 6.2 | 5.5 |
| $CO_2$ | 34.8 | 34.8 |

This Example shows a high CO conversion and high $C_2$-$C_3$ paraffins selectivity, combined with a high stability over time.

Example 25

A copper-chromium-zinc catalyst was prepared by following the co-precipitation method. A metal oxide catalyst component was prepared by adding 8.01 grams (g) of $Cu(NO_3)_2 \cdot 3H_2O$, 8.39 g of $Cr(NO_3)_3 \cdot 9H_2O$ and 13.65 g of $Zn(NO_3)_2 \cdot 6H_2O$ to distilled water ($H_2O$), targeting a total metal concentration of 1 mol/L. In addition, a 2 M solution of $(NH_4)_2CO_3$ was prepared as a precipitating agent. The metal oxide catalyst component mixture and the precipitating agent were simultaneously added dropwise to a stirred beaker containing 200 mL distilled $H_2O$ maintained at pH of about 7 and temperature of about 50° C., where the metal oxide catalyst precursor components co-precipitated out of the solution. The co-precipitated materials were filtered, washed with distilled water, dried in static air at 85° C. overnight, and subsequently calcined at 400° C. for 2 hours (h). The final catalyst had Cu, Cr, and Zn contents of 20.6, 26.9 and 52.5 atomic % based on the total metal content in the catalyst, respectively.

For a catalytic test, 1 gram of copper-chromium-zinc catalyst was physically mixed with 0.5 gram of a silicoaluminophosphate catalyst (SAPO-34) by gently shaking them together in a bottle to form a hybrid catalyst. Each of the catalysts had a particle size before mixing within a range of from 40 mesh (0.422 millimeter (mm)) to 80 mesh (0.178 mm). Prior to contacting the hybrid catalyst with syngas in the same reactor used in Example 1, the hybrid catalyst was reduced at 300° C. and atmospheric pressure for 6 hours by flowing 100 ml/min $H_2$. A catalytic performance test was carried out at 50 bar (5.0 MPa), 400° C. by flowing 20 ml/min CO, 11 ml/min $CO_2$, 64 ml/min $H_2$ and 5 ml/min He over the catalyst. The results are shown in Table 5 below.

TABLE 5

|  | 23 hrs on stream | 145 hrs on stream |
|---|---|---|
| Conversion [%] CO | 62 | 62 |
| Selectivity $C_1$ | 4.5 | 5.8 |
| $C_2$ | 20.6 | 19.5 |
| $C_3$ | 33.6 | 35 |
| $C_4$ | 10.6 | 11.7 |
| $C_5$ and higher | 6.6 | 4.7 |
| $CO_2$ | 24.1 | 23.3 |

This example shows that feed streams comprising $CO_2$ can be converted to desired products, showing stable CO conversion and high $C_2$-$C_3$ paraffin selectivity.

Comparative Example 36

A chromium-zinc mixed oxide catalyst was prepared by following the co-precipitation method. Targeting a Cr to Zn molar ratio of 0.4:1, 16.14 g of $Cr(NO_3)_3 \cdot 9H_2O$ and 29.97 g $Zn(NO_3)_2 \cdot 6H_2O$ were added to 20 mL of distilled water ($H_2O$). In addition, a 0.5 M solution of $(NH_4)_2CO_3$ was prepared as a precipitating agent. The metal nitrate and precipitating agent solutions were simultaneously added dropwise to a stirred beaker of distilled $H_2O$ maintained at a pH of about 7.0 and a temperature of 65+/−5° C. The co-precipitated materials were filtered, washed with distilled water, dried in static air at 120° C. overnight, and subsequently calcined at 600° C. for 2 h.

For a catalytic test, 1 gram of chromium-zinc catalyst was physically mixed with 0.5 gram of a silicoaluminophosphate catalyst (SAPO-34) by gently shaking them together in a bottle. Each of the catalysts had a particle size before mixing within a range of from 40 mesh (0.422 millimeter) to 80 mesh (0.178 millimeter). Prior to contacting with syngas, the catalyst was reduced at 400° C. and atmospheric pressure for 2 hours by flowing 22.5 ml/min $H_2$ and 11.25 ml/min $N_2$. Catalytic performance test was carried out at 50 bar (5.0 MPa), 400° C. by flowing 22.5 ml/min CO, 67.5 ml/min $H_2$ and 10 ml/min He over the catalyst. The results are shown in Table 6 below.

TABLE 6

|  | 23 hrs on stream | 145 hrs on stream |
|---|---|---|
| Conversion [%] CO | 59 | 58 |
| Selectivity $C_1$ | 8.7 | 10.6 |
| $C_2$ | 7.0 | 7.5 |
| $C_2=$ | 0.2 | 0.1 |
| $C_3$ | 31.7 | 30.8 |
| $C_3=$ | 0.7 | 0.3 |
| $C_4$ | 10.0 | 9.8 |
| $C_5$ and higher | 3.9 | 3.0 |
| $CO_2$ | 37.6 | 37.7 |

In Table 6, "=" indicates carbon with double bonds (i.e., olefins). Comparative Example 36 shows the low CO feed conversion obtained with Chromium-Zinc catalyst.

Comparative Example 37

Copper impregnated chromium-zinc catalyst (Cu/CrZn) was prepared by depositing 2.25 mL of a 1.95 mol/L $Cu(NO_3)_2 \cdot 3H_2O$ solution on 2.5 g of bulk Chromium-Zinc mixed oxide catalyst following the incipient wetness impregnation method. The final catalyst had Cu, Cr, and Zn contents of 14.9, 24.9 and 60.2 atomic % based on the total metal content in the catalyst, respectively. Chromium-zinc mixed oxide catalyst with a Cr to Zn molar ratio of 0.4:1 was prepared by following the co-precipitation method as described in Comparative Example 36.

For a catalytic test, 1 gram of copper impregnated chromium-zinc catalyst was physically mixed with 0.5 gram of a silicoaluminophosphate catalyst (SAPO-34) by gently shaking them together in a bottle. Prior to contacting with syngas, the catalyst was reduced at 400° C. and atmospheric pressure for 2 hours by flowing 22.5 ml/min $H_2$ and 11.25 ml/min $N_2$. Catalytic performance test was carried out at 50 bar (5.0 MPa), 400° C. by flowing 22.5 ml/min CO, 67.5 ml/min $H_2$ and 10 ml/min He over the catalyst. The results are shown in Table 7 below.

TABLE 7

|  | 23 hrs on stream | 145 hrs on stream |
|---|---|---|
| Conversion [%] CO | 71 | 56 |
| Selectivity $C_1$ | 6.7 | 9.6 |
| $C_2$ | 12.8 | 10.7 |
| $C_3$ | 28.9 | 26.3 |
| $C_3=$ | 0 | 0.2 |
| $C_4$ | 7.9 | 8.0 |
| $C_5$ and higher | 6.0 | 6.4 |
| $CO_2$ | 37.7 | 38.8 |

In Table 7, "=" indicates carbon with double bonds (i.e., olefins). Comparative Example 37 shows the poor stability of feed conversion obtained with Copper impregnated Chromium-Zinc catalyst.

Comparative Example 38

A physical mixture of a commercially available bulk copper-zinc oxide-alumina mixed metal oxide catalyst (HiFUEL® R120) and a chromium-zinc mixed metal oxide catalyst was prepared by gently shaking 0.0833 g of HiFUEL® and 0.1667 g of chromium-zinc catalyst in a glass vial. The chromium-zinc catalyst was prepared according the co-precipitation method described in Comparative Example 32. Each of the catalysts had a particle size before mixing within a range of from 40 mesh (0.422 millimeter) to 80 mesh (0.178 millimeter).

For a catalytic test, 0.25 gram of the mixed HiFUEL® and chromium-zinc catalyst were physically mixed with 0.75 gram of a silicoaluminophosphate catalyst (SAPO-34) by gently shaking them together in a bottle. Prior to contacting with syngas, the catalyst was reduced at 300° C. at atmospheric pressure for 6 hours by flowing 100 ml/min $H_2$. A catalytic performance test was carried out at 50 bar (5.0 MPa), 400° C. at various subsequent flow conditions as used for inventive examples 1-23 and comparative examples 1-35, as shown in Table 1, and outlined in the hydrocarbon productivity protocol.

A cumulative $C_2$ to $C_5$ Hydrocarbon productivity of 30 kg/kg Cat is obtained, which is lower than the productivity of at least 31.3 kg/kg Cat for CuCrZn(Al) inventive examples highlighted above, showing the clear benefit and necessity of incorporating all elements during catalyst synthesis (i.e. co-precipitation).

It will be apparent to those skilled in the art that various modifications and variations can be made to the embodiments described herein without departing from the spirit and scope of the claimed subject matter. Thus it is intended that the specification cover the modifications and variations of the various embodiments described herein provided such modification and variations come within the scope of the appended claims and their equivalents.

The invention claimed is:

1. A process for preparing $C_2$ to $C_5$ paraffins comprising:
   introducing a feed stream comprising hydrogen gas and a carbon-containing gas selected from the group consisting of carbon monoxide, carbon dioxide, and mixtures thereof into a reaction zone of a reactor; and
   converting the feed stream into a product stream comprising $C_2$ to $C_5$ paraffins in the reaction zone in the presence of a hybrid catalyst, the hybrid catalyst comprising:
   a metal oxide catalyst component comprising copper, chromium, and zinc; and a microporous catalyst component that is a molecular sieve having 8-MR pore openings, wherein
the metal oxide catalyst component satisfies:
an atomic ratio of Cu/Zn from 0.25 to 1.00;
an atomic ratio of Cr/Zn from 0.20 to 0.50; and
an atomic percentage of (Al+Cr) from 10.0 at % to 30.0 at % based on a total amount of metal in the metal oxide catalyst component.

2. The process for preparing C2 to C5 paraffins according to claim 1, wherein the metal oxide catalyst component further comprises aluminum.

3. The process for preparing C2 to C5 paraffins according to claim 1, wherein the feed stream comprises a combination of CO and CO2, and a ratio of CO2 to CO in the feed stream is from 0.1:1.0 to 0.7:1.0.

4. The process for preparing C2 to C5 paraffins according to claim 1, wherein a cumulative C2-C5 hydrocarbon productivity of the hybrid catalyst is greater than or equal to 31.3 kg/kg catalyst, measured according to the hydrocarbon productivity protocol.

5. The process for preparing C2 to C5 paraffins according to claim 1, wherein a cumulative C2-C5 hydrocarbon productivity of the hybrid catalyst is from 31.3 kg/kg cat to 60.0 kg/kg catalyst, measured according to the hydrocarbon productivity protocol.

6. The process for preparing C2 to C5 paraffins according to claim 1, wherein the microporous catalyst component is SAPO-34.

7. The process for preparing C2 to C5 paraffins according to claim 1, wherein converting the feed stream into a product stream comprising C2 to C5 paraffins comprises heating the reaction zone to a temperature from 300° C. to 500° C.

8. The process for preparing C2 to C5 paraffins according to claim 1, wherein converting the feed stream into a product stream comprising C2 to C5 paraffins occurs at a pressure of at least 20 bar.

* * * * *